US005712212A

United States Patent [19]
Scott et al.

[11] Patent Number: 5,712,212
[45] Date of Patent: Jan. 27, 1998

[54] APPARATUS AND METHOD FOR THE PRODUCTION OF GEL BEADS CONTAINING A BIOCATALYST

[75] Inventors: Charles D. Scott, Oak Ridge; Timothy C. Scott; Brian H. Davison, both of Knoxville, all of Tenn.

[73] Assignee: Lockheed Martin Energy Systems, Inc., Oak Ridge, Tenn.

[21] Appl. No.: 401,054

[22] Filed: Mar. 8, 1995

[51] Int. Cl.$^6$ .......................... B01D 37/36; C12N 11/04
[52] U.S. Cl. .................................. 502/7; 435/177
[58] Field of Search .......................... 502/7, 402, 403, 502/404; 435/177

[56] References Cited

U.S. PATENT DOCUMENTS

| | | | |
|---|---|---|---|
| 4,978,647 | 12/1990 | Scott et al. | 502/7 |
| 4,995,985 | 2/1991 | Scott et al. | 210/679 |

OTHER PUBLICATIONS

Marek P. J. Kierstan and Michael P. Coughlan, "Immobilization of Cells and Enzymes by Gel Entrapment," *Immobilized Cells and Enzymes: A Practical Approach*, IRL Press, Oxford (1985), pp. 39–48.

Charles D. Scott, "Techniques for Producing Monodispersed Biocatalyst Beads for Use in Columnar Reactors," *New York Acad. Sci.*, 501 (1987), pp. 487–493.

A. C. Hulst et al., "A New Technique for the Production of Immobilized Biocatalyst in Large Quantities," *Biotechnol. Bioeng.*, 27 (1985), pp. 870–876.

*Primary Examiner*—Glenn A. Caldarola
*Assistant Examiner*—Alexander G. Ghyka
*Attorney, Agent, or Firm*—Preston H. Smirman

[57] ABSTRACT

An apparatus and method for the large-scale and continuous production of gel beads containing a biocatalyst. The apparatus is a columnar system based on the chemical cross-linking of hydrocolloidal gels that contain and immobilize a biocatalyst, the biocatalyst being a microorganism or an enzyme. Hydrocolloidal gels, such as alginate, carrageenan, and a mixture of bone gelatin and modified alginate, provide immobilization matrices that can be used to entrap and retain the biocatalyst while allowing effective contact with substrates and release of products. Such immobilized biocatalysts are generally formulated into small spheres or beads that have high concentrations of the biocatalyst within the gel matrix. The columnar system includes a gel dispersion nozzle submerged in a heated non-interacting liquid, typically an organic liquid, that is immiscible with water to allow efficient formation of spherical gel droplets, the non-interacting liquid having a specific gravity that is less than water so that the gel droplets will fall through the liquid by the force of gravity. The heated non-interacting liquid is in direct contact with a chilled upflowing non-interacting liquid that will provide sufficient residence time for the gel droplets as they fall through the liquid so that they will be cooled below the gelling temperature and form solid spheres. The upflowing non-interacting liquid is in direct contact with an upflowing temperature-controlled aqueous solution containing the necessary chemicals for cross-linking or fixing of the gel beads to add the necessary stability. The flow rates of the two liquid streams can be varied to control the proper residence time in each liquid section to accommodate the production of gel beads of differing settling velocities. A valve is provided for continuous removal of the stabilized gel beads from the bottom of the column.

6 Claims, 1 Drawing Sheet

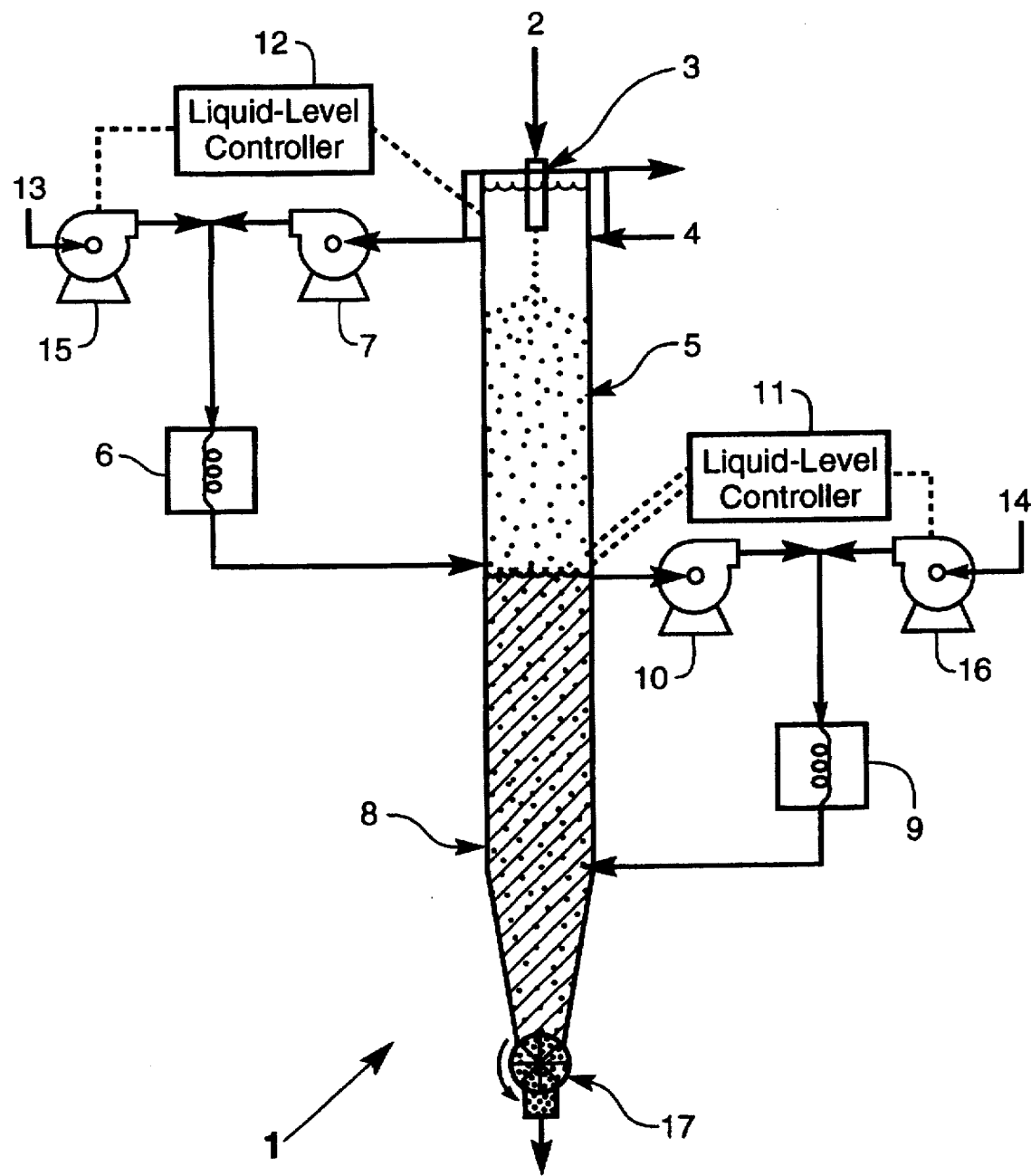
Figure

APPARATUS AND METHOD FOR THE PRODUCTION OF GEL BEADS CONTAINING A BIOCATALYST

This invention was made with Government support under contract DE-AC05-84OR21400 awarded by the U.S. Department of Energy, Advanced Bioprocessing Concepts Program to Martin Marietta Energy Systems, Inc. and the Government has certain rights in this invention.

FIELD OF THE INVENTION

The present invention relates generally to the immobilization of biocatalysts, and more particularly to an apparatus and method for the large-scale and continuous production of gel beads containing a biocatalyst.

BACKGROUND OF THE INVENTION

A biocatalyst is generally defined as a biochemical catalyst, especially microorganisms or isolated enzymes. Many advanced bioreactor concepts, especially those operating in a continuous mode (i.e., fluidized-bed bioreactors), require that the biocatalyst be retained within the bioreactor at a high concentration with excellent mass transfer and in an optimum environment. Since such biocatalyst material, when present as suspended organisms or dissolved macromolecules, has a tendency to be swept or carried out of the bioreactor by the liquid feed stream, it is necessary to immobilize the biocatalyst into or onto a solid support material that will not be unintentionally swept or carried out of the bioreactor.

One of the primary classes of immobilization materials or matrices are hydrocolloidal gels such as alginate, carrageenan, or bone gel. Other immobilization materials include synthetic polymers such as polyacrylamide, which are more difficult to manipulate. Gel material (also referred to as gelling material) refers specifically to hydrocolloidal gels, but may also refer to other cross-linking materials. These gelling materials can be used to entrap and retain the biocatalyst while allowing effective contact with substrates and release of products. Such immobilized biocatalysts are generally formulated into small spheres or beads that have high concentrations of the biocatalyst within the gel matrix. Conventionally, the standard technique consists of three main steps: (1) mix the gelling material (i.e., 4% κ-carrageenan) with the biocatalyst in an aqueous mixture at a temperature above the gelling point but within the range of biocatalyst viability (this mixture is then forced through a nozzle or orifice with sufficient force to form droplets); (2) the droplets are then allowed to cool below the gelling temperature, usually by air cooling as they (3) fall into an aqueous fixing solution where chemical cross-linking occurs after an adequate contacting time. The cross-linking results in a stable biocatalyst gel bead that can be used in the bioreactor system.

All of these steps are currently carried out on a laboratory scale, in a batch or semibatch mode with a significant amount of hand labor. Therefore, it would be desirable to produce large quantities of the gel beads containing a biocatalyst in an apparatus that accommodates the necessary processing steps on a rapid and continuous basis. Of particular interest, is the rapid cooling of the liquid droplets, contact with the fixing solution for an adequate amount of time, and disengagement of the stable gel beads, all on a continuous basis. Additionally, it is desirable to assure rapid and complete solidification (gelling) of the droplet prior to cross-linking so it will not be easily distorted into a non-spherical shape or tend to aggregate. It is also important to be able to produce relatively large quantities of the beads with minimal operator attention and on a continuous basis. The present invention claims an apparatus and method which utilizes an integrated approach to these three main processing steps.

OBJECTS OF THE INVENTION

Accordingly, it is an object of the present invention to provide a new and improved method for the immobilization of biocatalysts.

It is another object of the present invention to provide a new and improved method for the production of gel beads containing a biocatalyst.

It is another object of the present invention to provide a new and improved apparatus for the immobilization of biocatalysts.

It is another object of the present invention to provide a new and improved apparatus for the production of gel beads containing a biocatalyst.

Further and other objects of the present invention will become apparent from the description contained herein.

SUMMARY OF THE INVENTION

In accordance with one aspect of the present invention, the foregoing and other objects are achieved by:

mixing a biocatalyst with an aqueous gel solution to form an aqueous biocatalyst-gel solution, the aqueous biocatalyst-gel solution being maintained at a temperature sufficient to prevent solidification, the aqueous biocatalyst-gel solution being maintained at a temperature which is within the viability range of the biocatalyst, the aqueous gel solution containing a gelling material;

providing a vessel, the vessel having at least one inlet and at least one outlet, the vessel containing a non-interacting liquid phase and an aqueous liquid phase, the non-interacting liquid phase having a lower specific gravity than the aqueous liquid phase, the non-interacting liquid phase consisting of an upper region and a lower region;

introducing the aqueous biocatalyst-gel solution in droplet form into the upper region of the non-interacting liquid phase, the upper region of the non-interacting liquid phase being maintained at a temperature sufficient to prevent the solidification of the aqueous gel-biocatalyst solution, the droplet descending downwardly through the lower region of the non-interacting liquid phase, the lower region of the non-interacting liquid phase being maintained at a temperature below the gelling temperature of the aqueous gel-biocatalyst solution so as to cause the droplet to solidify into a gel bead;

introducing the gel bead into the aqueous liquid phase, the gel bead descending downwardly through the aqueous liquid phase, the aqueous liquid phase containing a fixing solution so as to cause a cross-linking reaction to occur, the aqueous liquid phase being maintained at a temperature below the gelling temperature of the aqueous gel-biocatalyst solution; and recovering the gel bead.

In accordance with another aspect of the present invention, the foregoing and other objects are achieved by:

a vessel, the vessel having at least one inlet and at least one outlet, the vessel containing an aqueous liquid phase and a non-interacting liquid phase, the non-interacting liquid phase having a lower specific gravity than the aqueous liquid phase, the non-interacting liquid phase consisting of an upper region and a lower region;

first introducing means for introducing the aqueous liquid phase into the vessel;

second introducing means for introducing the non-interacting liquid phase into the vessel;

third introducing means for introducing an aqueous biocatalyst-gel solution in droplet form into the upper region of the non-interacting liquid phase, the aqueous biocatalyst-gel solution containing a gelling material, the lower region of the non-interacting liquid phase being maintained at a lower temperature than the aqueous biocatalyst-gel droplet so as to cause the aqueous biocatalyst gel droplet to solidify into a gel bead;

fixing means for allowing a cross-linking reaction to occur;

first temperature adjustment means for adjusting the temperature of the aqueous liquid phase;

second temperature adjustment means for adjusting the temperature of the non-interacting liquid phase;

liquid level adjustment means for adjusting the liquid level of the aqueous liquid phase and the non-interacting liquid phase;

first removal means for removing the aqueous liquid phase;

second removal means for removing the non-interacting liquid phase; and third removal means for removing the gel bead.

BRIEF DESCRIPTION OF THE DRAWING

The FIGURE illustrates an apparatus in accordance with one embodiment of the present invention.

DETAILED DESCRIPTION

The continuous and large-scale production of gel beads containing a biocatalyst utilizing hydrocolloidal gelling material (such as alginate, carrageenan, or bone gelatin mixture) will require several sequential processing steps: (1) the gelling or immobilization material (generally 4–20 wt %) and the biocatalyst are mixed in an aqueous solution at a temperature sufficiently high to prevent gelling but within the range of biocatalyst viability (e.g. 40° C.); (2) this mixture is then dispersed into liquid droplets; (3) the droplets are cooled below the gelling temperature (generally 25° to 35° C.) to form spherical gel beads; (4) the gel beads are contacted with a chemical cross-linking or fixing solution (e.g., 0.2M $CaCl_2$ for sodium alginate, 2 wt % KCl for ι-carrageenan, and 0.01N NaOH for a mixture of bone gelatin and modified alginate) for 20 to 60 minutes; and (5) final segregation of the gel beads from the bulk of the fixing solution. It should be noted that the present invention can be practiced with any type of gelling material, biocatalyst, or gel shape (i.e., the gel does not necessarily have to possess a spherical shape).

With reference to the FIGURE, one embodiment of the present invention utilizes a generally columnar shaped bioreactor 1 (also referred to as a vessel) in which the heated gel solution 2 containing the biocatalyst is dispersed into droplets by flow through a nozzle 3 or orifice or plurality of nozzles or orifices, utilizing imposed sonic vibrations or other available techniques to enhance the dispersion process, if necessary. It is important to cool the gel droplets below the gelling or solidification temperature so that the gel beads are relatively stable before they contact the aqueous interface where chemical cross-linking is carried out. To achieve that, the droplets are actually formed in a non-interacting liquid (typically an organic liquid) where the cooling can be substantially carried out as the droplets fall through the liquid. The non-interacting liquid should have a specific gravity less than 1.0 since the aqueous-phase droplets should preferably fall through the noninteracting liquid by the force of gravity. It is also preferable for the non-interacting liquid to be immiscible with water and nondetrimental to the biocatalyst since it will be in contact with the aqueous fixing solution.

An upper heated section 4 (also referred to as the upper non-interacting organic liquid phase or region) containing the non-interacting liquid substantially surrounds the nozzle 3, thus, maintaining the nozzle 3 at or near the entering gel solution temperature. This was found necessary to prevent the plugging of the nozzle 3. Further, the cooled non-interacting organic medium 5 (also referred to as the lower non-interacting organic liquid phase or region) directly below the heated section 4 is provided by a circulating cooler 6 that introduces an upflow of the liquid. This can also be achieved by cooling the contents of that section of the column by an external cooling jacket for temperature control and the use of a circulation pump 7 to maintain an upward velocity of the cooled noninteracting organic liquid 5. The upward flow of this cooled non-interacting organic liquid 5 (both the upper and lower non-interacting organic phases are also referred to as the non-interacting organic phase, the non-interacting organic medium, the non-interacting organic section, or the non-interacting organic liquid) provides the necessary cooling for gelling or solidification of the droplet, but also it can be used to retard the downward progression of the resulting beads, thus, allowing control over the amount of residence time in the cooled non-interacting organic region 5. This has been found superior to simply adding more column height with the necessary additional external cooling and noninteracting liquid. The temperature of the cooling liquid, typically 10° to 20° C., must be lower than the gelling temperature of the aqueous biocatalyst-gel solution which is typically 25° to 35° C.

The cooled non-interacting organic liquid 5 is in direct contact with the aqueous fixing solution 8 (also referred to as the cross-linking solution, the aqueous section, the aqueous region, the aqueous phase, or the aqueous liquid), thus allowing the gel beads to profess through the interface and fall directly into this aqueous liquid. The aqueous fixing solution 8 is also maintained at a temperature below the gelling temperature, but not so low that the chemical cross-linking reaction is seriously affected (typically 15° to 25° C.). The beads fall through the aqueous section in which the temperature is controlled by the upflow of the liquid from an external heater/cooler 9, or alternatively, an external cooling jacket with liquid circulator, such as a circulating pump 10. As in the case of the organic liquid section, the flow of the aqueous fixing solution 8 up the column can also be used to control the amount of residence time of the biocatalyst in the aqueous phase. As the cross-linking reaction occurs, the gelling material of the gel bead cross-links with the appropriate chemical constituent in the aqueous solution. The cross-linked and stabilized gel beads ultimately fall to the bottom of the bioreactor 1 where they may be removed by a rotating valve 17 (or any other suitable removal means) that is divided into multiple segments by a series of equal-distance radial vanes (multivaned valve).

The main utility of using upflow of both the non-interacting liquid and the cross-linking solution is that a much shorter column section can be used while maintaining adequate residence time in the liquids. Also, if it is desired to form gel beads with different settling velocities (i.e., different diameter or specific gravity), the column does not have to be restructured (change in column height), but rather the flow rates of the liquids need only be changed. Thus, this type of apparatus would have general utility for a variety of gel formulations and sizes, while still providing continues operation.

It is preferable to maintain both the top liquid level and the interfacial liquid levels within generally narrow limits (i.e., +1 cm) by replacing the liquids as they are lost from the system. Some aqueous liquid will exit with the gel beads and a small amount of the non-interacting organic liquid may be entrained in the aqueous phase. Control of these levels will ensure that the nozzle exit remains covered with the non-interacting organic phase and the liquid-liquid interface is kept between the entrance point of the circulating organic liquid and the exit point of the aqueous fixing solution. Although a e, se can be controlled manually with periodic addition of the liquids, it is preferable to use liquid level controllers 11 and 12 connected to make-up reservoirs 13 (organic liquid) and 14 (crosslinking solution) for this purpose. The makeup reservoirs utilize make-up pumps 15 and 16 to introduce additional organic liquid and cross-linking solution into the bioreactor 1. Conductivity probes can be used for controlling the interfacial level and a simple float detector can be used to sense the organic liquid level. It would also be preferable to control the various bioreactor parameters with a computer. The computer can automatically control the addition or removal of various liquids, maintain proper interfacial levels, control the removal of the gel beads, maintain and adjust temperature levels, as well as any other necessary functions.

An example of the large-scale and continuous production of gel beads containing a biocatalyst, in accordance with one embodiment of the present invention, is presented below:

EXAMPLE

A test was made in which an apparatus similar to that shown in the FIGURE was used. The column was 6 inch-diameter glass pipe vertically mounted with a 3 foot section containing light mineral oil (J. T. Baker, Inc.™, Phillipsburg, N.J.) and a 3 foot section containing the aqueous cross-linking liquid which was 0.3M KCl (Fisher Scientific™, Fair Lawn, N.J.). The bottom of the column was a section of glass pipe that tapered down from 6 inch-diameter to 0.5 inch-diameter at which point it was connected to a rotating, multivaned valve. The upper 6 inches of the column was heated externally to a temperature of 40° C., the next 3 foot section was cooled to 10° C. by an external cooling jacket using a temperature-controlled cooling circulator (Model 1150, VWR Scientific™, Philadelphia, Pa.), and the bottom section of the column was maintained at 25° C. by an external jacket utilizing a heater/circulator (Polystat Circulator™, Model 12105-00, Cole Parmer Instrument Co.™, Niles, Ill.). The aqueous cross-linking liquid and the light mineral oil were individually circulated by peristaltic pumps (MasterFlex™, Cole Parmer Instrument Co.™, Niles, Ill.) and make-up liquids were manually introduced through a port in the top of the column. The stabilized biocatalyst beads were continuously removed with a 2 inch-diameter multivaned bottom valve with the four stainless steel radial vanes mounted on an internal shaft and in contact with a Teflon™ body. The shaft rotated at approximately 2 revolutions per minute. The gelling solution was 4 wt % ι-carrageenan (FMC Corp.™, Springfield, N.J.) in water with 3 wt % $Fe_2O_3$ particles for control of specific gravity and approximately 10 vol % $Zymomonas$ $mobilis$. This slurry was maintained at 40° C. and forced through a 0.58-mm-ID nozzle by a MasterFlex™ pump. As described in a previous publication, a sonic vibrator (Model OC-25, Alpha-M Corp™, Dallas, Tex.) was attached to the tubing used to deliver the gel slurry to the nozzle and vibration at a frequency of 260 Hz was used to assist in disengaging the gel droplets from the nozzle tip. The flow rate of the circulating mineral oil was maintained to give an upward liquid velocity of approximately 0.01 mm/second and that of the aqueous solution was maintained to give an upward liquid velocity of approximately 0.05 mm/second. This resulted in an approximate residence time of 10 minutes in the cooling organic section and 25 minutes in the aqueous section for chemical cross-linking. The single nozzle produced biocatalyst beads of approximately 1.5-mm-diameter at a rate of approximately 2 liters/hour.

The present invention could be used for any solidification process in which there was an initial temperature-dependent solidification followed by a chemical stabilization step. The present invention is expected to have broad applications in large-scale bioconversion processes and especially those using a fermentation step. The present invention should be particularly useful in processes for the bioconversion of renewable feedstocks to fuels and chemicals, as well as having applications in the pharmaceutical industry.

While there has been shown and described what are at present considered the preferred embodiments of the invention, it will be obvious to those skilled in the art that various changes and modifications can be made therein without departing from the scope of the invention defined by the appended claims.

What is claimed is:

1. A method of manufacturing a gel bead containing a biocatalyst, comprising the steps of:

mixing the biocatalyst with an aqueous gel solution to form an aqueous biocatalyst-gel solution, the aqueous biocatalyst-gel solution being maintained at a temperature sufficient to prevent solidification, the aqueous biocatalyst-gel solution being maintained at a temperature which is within the viability range of the biocatalyst, the aqueous gel solution containing a gelling material;

providing a vessel, the vessel having at least one inlet and at least one outlet, the vessel containing a non-interacting liquid phase and an aqueous liquid phase, the non-interacting liquid phase having a lower specific gravity than the aqueous liquid phase, the non-interacting liquid phase consisting of an upper region and a lower region, the non-interacting liquid phase and the aqueous liquid phase being continuously introduced into the vessel, the non-interacting liquid phase and the aqueous liquid phase being continuously removed from the vessel;

introducing the aqueous biocatalyst-gel solution in droplet form into the upper region of the non-interacting liquid phase, the upper region of the non-interacting liquid phase being maintained at a temperature sufficient to prevent the solidification of the aqueous gel-biocatalyst solution, the droplet descending downwardly through the lower region of the non-interacting liquid phase, the lower region of the non-interacting liquid phase being maintained at a temperature below the gelling temperature of the aqueous gel-biocatalyst solution so as to cause the droplet to solidify into a gel bead;

introducing the gel bead into the aqueous liquid phase, the gel bead descending downwardly through the aqueous liquid phase, the aqueous liquid phase containing a fixing solution so as to cause a cross-linking reaction to occur, the aqueous liquid phase being maintained at a temperature below the gelling temperature of the aqueous gel-biocatalyst solution; and recovering the gel bead.

2. A method in accordance with claim 1, wherein the gelling temperature of the aqueous biocatalyst-gel solution is in the range of about 25° C. to about 35° C.

3. A method in accordance with claim 1, wherein the temperature of the aqueous liquid phase is in a range sufficient to allow the cross-linking reaction to occur.

4. A method in accordance with claim 1, wherein the aqueous liquid phase is flowing in an upwardly manner.

5. A method in accordance with claim 1, wherein the non-interacting liquid phase is flowing in an upwardly manner.

6. A method in accordance with claim 1, wherein the non-interacting liquid phase comprises an organic liquid.

* * * * *